(12) United States Patent
Huq et al.

(10) Patent No.: US 7,775,084 B2
(45) Date of Patent: Aug. 17, 2010

(54) FLUID PROBE

(75) Inventors: Ejaz Huq, Daresbury (GB); Vladislav Djakov, Daresbury (GB); Paul Vernon, Daresbury (GB)

(73) Assignee: Council for the Central Laboratory of the Research Councils, Warrington (GB)

( * ) Notice: Subject to any disclaimer, the term of this patent is extended or adjusted under 35 U.S.C. 154(b) by 164 days.

(21) Appl. No.: 10/596,208

(22) PCT Filed: Dec. 3, 2004

(86) PCT No.: PCT/GB2004/005079

§ 371 (c)(1),
(2), (4) Date: Jun. 2, 2006

(87) PCT Pub. No.: WO2005/054817

PCT Pub. Date: Jun. 16, 2005

(65) Prior Publication Data
US 2008/0028837 A1    Feb. 7, 2008

(30) Foreign Application Priority Data
Dec. 4, 2003    (GB) .............................. 0328054.2

(51) Int. Cl.
*G01N 11/10* (2006.01)

(52) U.S. Cl. ..................... 73/54.27; 73/54.24

(58) Field of Classification Search ................ 73/54.38, 73/54.23, 54.24, 54.25, 54.26, 54.32, 54.27
See application file for complete search history.

(56) References Cited

U.S. PATENT DOCUMENTS

| | | | |
|---|---|---|---|
| 4,695,956 A | 9/1987 | LeVeen et al. | |
| 5,780,727 A | 7/1998 | Gimzewski et al. | |
| 6,044,694 A | 4/2000 | Anderson et al. | |
| 6,182,499 B1 * | 2/2001 | McFarland et al. | ............ 506/12 |
| 6,249,001 B1 | 6/2001 | Sauer et al. | |

(Continued)

FOREIGN PATENT DOCUMENTS

GB    2359368    8/2001

(Continued)

OTHER PUBLICATIONS

Coutinho, Murilo G., Will, Peter M., Viswanathan, P. Selvan. "The Intelligent Motion Surface: A hardware/software tool for the assembly of meso-scale devices" IEEE, Albuquerque, New Mexico, 1997.*

(Continued)

*Primary Examiner*—John Fitzgerald
(74) *Attorney, Agent, or Firm*—John V. Daniluck; Bingham McHale LLP

(57) ABSTRACT

A device for detecting a property of a fluid includes a body region and a flexible element having a first end and a second end. The first end is fixedly located on the body region. The flexible element is arranged to move from at least a first configuration to a second configuration via bending of the flexible element. The flexible element includes an actuating portion arranged to move the flexible element between the first configuration and the second configuration. The device also includes a movement detector for detecting movement of the flexible element.

27 Claims, 5 Drawing Sheets

U.S. PATENT DOCUMENTS

| | | | |
|---|---|---|---|
| 6,260,408 B1 * | 7/2001 | Vig et al. | 73/64.53 |
| 6,269,685 B1 * | 8/2001 | Oden | 73/54.23 |
| 6,269,686 B1 | 8/2001 | Hahn et al. | |
| 6,311,549 B1 * | 11/2001 | Thundat et al. | 73/54.24 |
| 6,436,647 B1 | 8/2002 | Quate et al. | |
| 6,457,360 B1 * | 10/2002 | Daraktchiev et al. | 73/579 |
| 6,575,020 B1 * | 6/2003 | de Charmoy Grey et al. | 73/54.23 |
| 7,047,794 B2 * | 5/2006 | Hajduk et al. | 73/54.37 |
| 2003/0056574 A1 * | 3/2003 | Drahm et al. | 73/54.04 |
| 2003/0062193 A1 | 4/2003 | Thaysen et al. | |
| 2007/0272002 A1 * | 11/2007 | Jakoby | 73/54.26 |
| 2008/0011058 A1 * | 1/2008 | Lal et al. | 73/54.23 |

FOREIGN PATENT DOCUMENTS

| | | |
|---|---|---|
| GB | 2369887 | 6/2002 |
| WO | WO0066266 | 11/2000 |
| WO | 03022731 | 3/2003 |
| WO | 03062135 | 7/2003 |
| WO | 03067248 | 8/2003 |
| WO | 03071258 | 8/2003 |
| WO | 03104784 | 12/2003 |
| WO | 2004059306 | 7/2004 |
| WO | 2004083802 | 9/2004 |

OTHER PUBLICATIONS

Notification Concerning Transmittal of International Preliminary Report on Patentability, Chapter I of the Patent Cooperation Treaty, and Written Opinion of the International Searching Authority, dated Nov. 14, 2006, for PCT/JP2005/008755, 4 sheets.

Thaysen, J. et al., "SU-8 Based Piezoresistive Mechanical Sensor," The Fifteenth IEEE Internal conference on Micro Electro Mechanical Systems, 2002, Las Vegas, pp. 320-323.

Djakov, V. et al., "Bimorph Actuators for MOEMS," Proc. SPIE vol. 4755, p. 804-814, Design, Test, Integration, and Packaging of MEMS/MOEMS 2002.

Coutinho, M.G. et al., "The Intelligent Motion Surface: A hardware/software tool for the assembly of meso-scale devices," IEEE International Conference on Robotics and Automation, Albuquerque, NM, 1997.

Suh, J.W. et al., "Organic thermal and electrostatic ciliary micractuator array for object manipulation," Sensors and Actuators A 58 (1997), pp. 51-60.

Riethmuller, W. et al., "Thermally Excited Silicon Microactuators," IEEE Transactions on Electron Devices, vol. 35: No. 6, Jun. 1988.

Ataka, M. et al., "Fabrication and Operation of Polyimide Bimorph Actuators for a Ciliary Motion System," Journal of Microelectromechanical Systems, vol. 2: No. 4, Dec. 1993.

Que, Lon et al; "Bent-Beam Electrothermal Actuators—Part I: Single Beam and Cascaded Devices," Journal of Microelectromechanical Systems, vol. 10, No. 2, Jun. 2001.

\* cited by examiner

FLUID PROBE

CROSS REFERENCE TO RELATED APPLICATIONS

This application is the national stage of International Patent Application PCT/GB2004/005079, filed Dec. 3, 2004 (which was published in English), which claims the benefit of priority to British Patent Application No. 0328054.2, filed Dec. 4, 2003.

This invention relates to the determination of properties of fluids, and in particular is suitable for, although not restricted to, the determination of the viscosity of fluids such as blood.

Determining the properties of a fluid is crucial in a wide range of industries. For example it is important to know the viscosity of oil in the oil industry and the temperature of milk in a dairy. Measurements can be taken continuously in real time, or at specific times, either with an appropriate 'in-situ' sensor, or by placing an appropriate sensor into the fluid of interest and then taking a reading.

An important property of many fluids is its viscosity. For example, the viscosity of the blood is crucial to the determination of the blood pressure of the patient. Furthermore, by continuous monitoring of a blood sample, the rate of clotting can be determined. The clotting rate of a patient's blood can be used to diagnose certain conditions, such as deep vein thrombosis.

Current devices used for measuring viscosity ('viscometers' or "viscosimeters") have a number of disadvantages. The devices are generally large, bulky and expensive to both purchase and manufacture.

If a fluid sample is valuable, for example economically (a new medicine) or otherwise (the blood of a patient), it is undesirable to use and possibly waste large amounts of that sample in determining its properties. Due to the large size of state of the art viscometers, a correspondingly large fluid sample has to be utilised. Furthermore, it is often necessary to take a sample from its local environment in order to undertake a measurement. In doing so, stabilising agents often have to be added to the sample so as to prevent the measurements of the sample being adversely affected during transport from the sampling site to the viscometer. For example, coagulants are added to blood when retrieved from a patient so as to prevent the blood from clotting when exposed to air. Any addition of such an agent contaminates or reduces the purity of the sample, often affecting its properties and is thus undesirable. Ideally, measurements should be taken either in-situ, or without the need for addition of agents.

According to a first aspect of the present invention, there is provided a method of determining a property of a fluid using a sensing element comprising a flexible element movable from a first configuration to a second configuration via bending of the flexible element, the flexible element comprising an actuating portion arranged to move the flexible element between the first configuration and the second configuration, the method comprising inducing movement in the flexible element between the first configuration and the second configuration by applying a heat signal to the flexible element, receiving a signal from the sensing element, the signal being indicative of movement of the flexible element within the fluid and processing the signal to determine a value indicative of at least one property of the fluid.

The inventors have realised that such a method can be used to measure the viscosity, shear, flow rate or temperature of a fluid simply by using a heat signal to move the flexible element. Furthermore, the sensing element can be constructed so as to be of dimensions of the order of micrometers. Hence, in-situ or on location measurements can be made of extremely small samples, negating the need for addition of stabilising agents.

Most preferably, the signal is processed to determine a value indicative of at least one property of a group comprising viscosity, temperature, flow rate and shear rate.

The method may further comprise determining a rate of change of movement of the flexible element, by monitoring a change in the received signal with time and determining a value indicative of the viscosity of the fluid from the rate of change of movement.

The method may further comprise determining an amplitude of movement of the flexible element from the received signal for a given applied heat signal and determining a value indicative of the viscosity of the fluid from the amplitude.

The method may further comprise the step of determining the resonant frequency of the flexible element in the fluid by applying a plurality of different frequency heat signals to the sensing element, monitoring the amplitude of movement of the flexible element from the received signal to identify a resonant frequency of the flexible element and determining a value indicative of the viscosity of the fluid from the identified resonant frequency.

The method may further comprise determining a change in the movement of the flexible element and determining a value indicative of a flow rate of the fluid from the change in movement, the change in movement being due to flow of the fluid against the flexible element.

The method may further comprise determining a value indicative of a shear rate of the fluid by determination of the flow rate at a plurality of locations within the fluid.

The actuating portion of the flexible element may comprise a laminate of at least two layers, each layer having a different coefficient of thermal expansion, and wherein the method may then further comprise, prior to induction of movement by application of the heat signal, determining a value indicative of the temperature of the fluid.

The device may comprise a plurality of flexible elements, and the method may further comprise using the plurality of flexible elements to determine a value indicative of at least one property of the fluid in a plurality of locations.

The device may comprise a plurality of flexible elements, and the method may further comprise using at least one of the plurality to cause a flow within the fluid, and using at least one of the plurality to determine a value indicative of at least one property of said fluid.

The method may further comprise holding the flexible element in at least one of said two configurations by a magnetic force. Alternatively, the method may further comprise holding the flexible element in at least one of said two configurations by an electrostatic force.

According to a second aspect of the present invention, there is provided a device for detecting a property of a fluid comprising a body region, a flexible element having a first end and a second end, the first end being fixedly located on the body region, the flexible element being arranged to move from at least a first configuration to a second configuration via bending of the flexible element, the flexible element comprising a laminate of at least two layers and an actuating portion arranged to move the flexible element between the first configuration and the second configuration, the actuating portion being provided by at least a first layer of the laminate having a different coefficient of thermal expansion from a second layer of the laminate such that a change in temperature of the flexible element moves the flexible element from the first configuration to the second configuration, the flexible element further comprising a heating element for heating at least the flexible element thereby providing the change in temperature, and a movement detector arranged to detect the movement of the flexible element, and to provide a signal indicative of a property of a fluid in which the flexible element is immersed.

Preferably, the movement detector is arranged such that an electrical property of the movement detector changes due to movement of the flexible element. Most preferably, the movement detector comprises a piezoresistive element located on the flexible element arranged such that the electrical resistance of the piezoresistive element changes due to movement of the flexible element.

The movement detector may comprise a capacitor having two plates, the flexible element forming one plate thereof, and an electrically conducting plate forming the other plate, such that the capacitance of the capacitor changes due to movement of the flexible element.

The device may comprise latching means arranged to hold the flexible element in at least one of the two configurations.

The movement detector may comprise an electromagnetic radiation source arranged to direct radiation towards the element, and an electromagnetic radiation detector arranged to detect electromagnetic radiation at least one of: reflected from, transmitted through, refracted from or diffracted by the flexible element.

Most preferably, the first layer of the laminate comprises a polymer. The first layer of the laminate may comprise a material selected from a group consisting of polyimides, polyamides and acrylic polymers. The second layer may comprise a polymer. The second layer may comprise a material selected from a group consisting of polyimides, polyamides and acrylic polymers.

Most preferably, the second layer of the laminate comprises a metal. The metal may be selected from a group consisting of gold or aluminium.

Preferably, the length of the flexible element from the first to the second end is between 100 µm and 1 mm, and the distance between the second end of the flexible element in said first configuration and the second end of the flexible element in said second configuration is between 30 µm and 650 µm.

The device may comprise a plurality of flexible elements. Preferably, the plurality of flexible elements are arranged in a first row and a second row, each row comprising at least one flexible element, the flexible elements being arranged such that the at least one flexible element of the first row extends in opposition to the at least one flexible element of second row. Most preferably, the plurality of the flexible elements are interdigitated.

Embodiments of the invention will now be described by way of example with reference to the accompanying figures in which.

Figure 1:
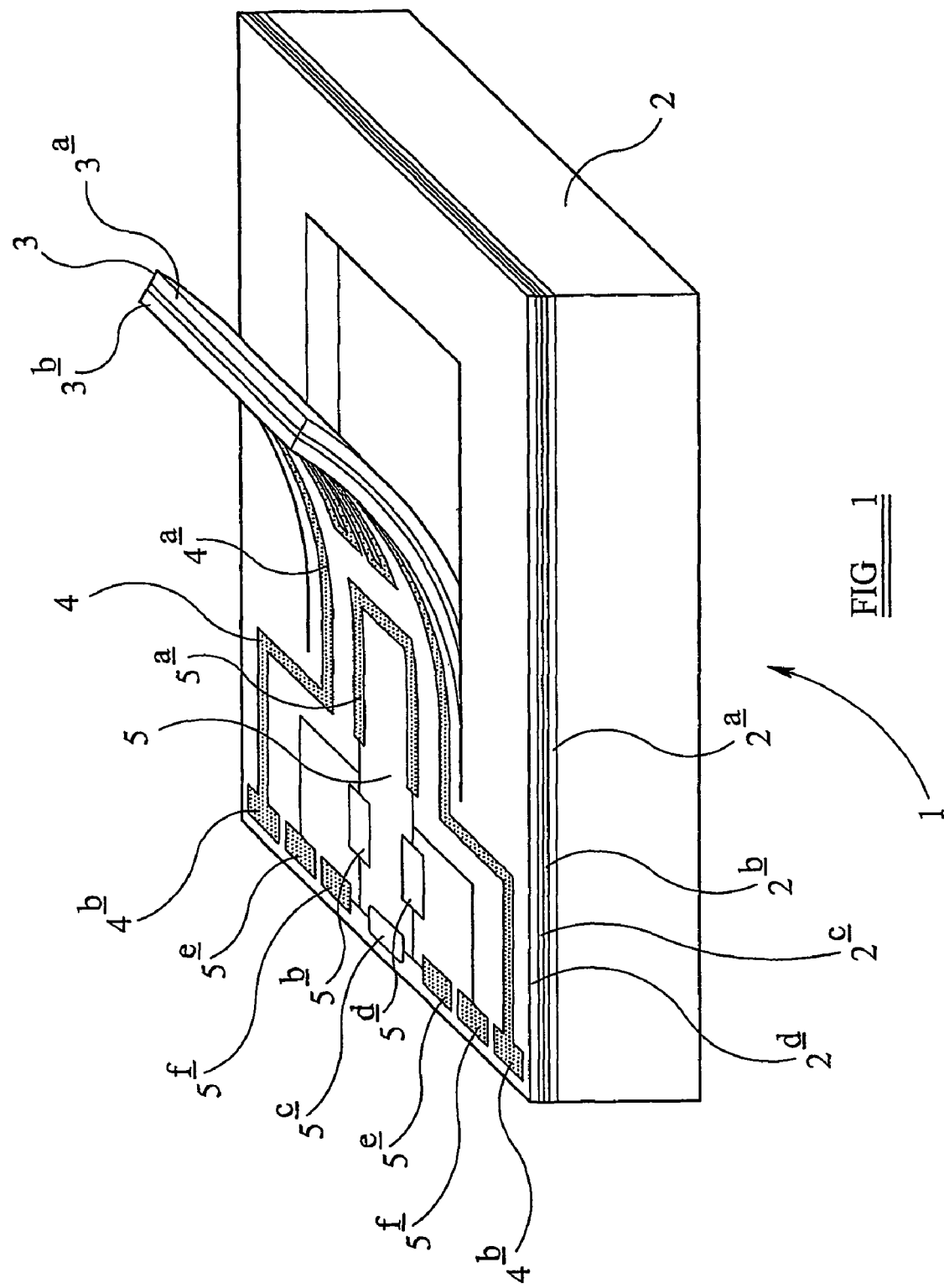
FIG. 1 is a perspective view of a detection device in accordance with a preferred embodiment of the invention.

Illustrated in FIG. 1 is a perspective view of a detection device 1 according to a preferred embodiment of the present invention. The detection device 1 comprises a body region 2, a flexible element 3, a heater 4 and a Wheatstone bridge circuit 5.

The flexible element 3 is an integral part of and extends from the body region 2. The first end of the flexible element is connected to the body region. The second end of the flexible element, distance from the first, is free to move in relation to the body region. The flexible element is a bar with a rectangular surface area, with the longer side of the rectangle extending from the body region. The flexible element 3 comprises a laminate of two layers 3a, 3b, the materials of each layer having different coefficients of thermal expansion. The materials can be different materials, or the same material processed (e.g. stressed) so as to have different coefficients of thermal expansion.

Under application of heat, one layer will expand more than the other for the same rise in temperature, and hence the flexible element 3 will bend in the direction of the material with the lower coefficient of thermal expansion. Upon cooling, one layer will contract faster than another for the same decrease in temperature, and hence the flexible element 3 will then bend in the direction of the material with the greater coefficient of thermal expansion.

The heater 4 is located on the flexible element 3, and comprises conductive material forming a continuous line or track 4a across an area of the upper surface of the flexible element 3. The heater 4 further comprises electrical contacts 4b for delivery of current to (and resulting in heat dissipation from) the heater 4. These electrical contacts 4b are located on an upper surface of the body region 2.

Figure 2:
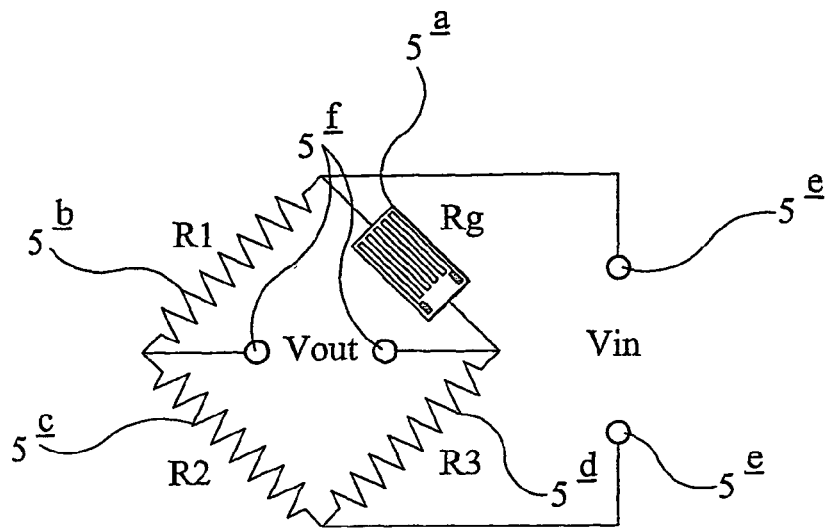
FIG. 2 is a circuit diagram of a Wheatstone bridge circuit forming part of the device shown in FIG. 1.

Wheatstone bridge circuits 5 are well known in the art as being particularly sensitive apparatus for the measurement of capacitance and resistance. A Wheatstone bridge circuit 5 is located on the body region 2 and flexible element 3. The Wheatstone bridge 5 comprises four 'legs' or 'arms' 5a, 5b, 5c, 5d, three of which 5b, 5c, 5d, reside on the body region 2, and one of which 5a resides on the flexible element 3 immediately adjacent the body region 2. The three legs 5b, 5c, 5d residing on the body region 2 each comprise a resistance of a known value. The fourth leg 5a, residing on the flexible element 3, comprises a piezoresistive element 5a. A piezoresistive material is one whose electrical resistance changes upon the application thereon of mechanical strain. Furthermore, the Wheatstone bridge circuit 5 comprises electrical contacts 5e, 5f on an upper surface of the body region 2 for input and output of electrical signals. The Wheatstone bridge circuit 5 is illustrated in FIG. 2.

In use, a voltage is applied across the Wheatstone bridge circuit 5 via contacts 5e, and a voltage output is measured across the middle from contacts 5f. When the output of the bridge 5 is zero, the bridge 5 is said to be balanced and the resistances equal.

When the resistance of one of the legs 5a, 5b, 5c, 5d, changes, the previously balanced bridge 5 is now unbalanced. This unbalance causes a voltage to appear across the middle of the bridge 5. From this value, the change in resistance can be calculated. However, the bridge 5 need not be balanced initially. Although the initial output voltage may then be non-zero in magnitude, the non-zero value can be used as a relative zero value. The only substantial variation in resistance of the Wheatstone bridge 5 will arise from the piezoresistive element, thus it can be assumed that any substantial variation in voltage output is attributed to the movement of the flexible element 3. Preferably the three known resistances are identical and in close proximity to compensate for any temperature variations etc.

Surface micro machining of thin films can be used to construct the device shown in FIG. 1. In a preferred embodiment, polyimide and gold films are used to produce the flexible element 3. Polyimide (DuPont, Pyralene PI2566) is chosen for its high coefficient of thermal expansion ($60 \times 10^{-6}$ $K^{-1}$) and small Young's modulus (1.75 GPa), allowing large displacements with small change in temperature. Also, polyimide films can be easily spin-coated from the liquid phase allowing a range of thickness to be tested for optimum deflection. Many other plastic polymers can be used, also spin coated in their liquid phase, such as PI2722, PI2723 (both of which have a coefficient of thermal expansion of $57 \times 10^{-6}$ $K^{-1}$) or PI2734 (coefficient of thermal expansion of $13 \times 10^{-6}$ $K^{-1}$). Gold was chosen because of its appropriate mechanical and thermal properties with respect to the PI2566 polyimide. For example, gold has a considerably lower coefficient of thermal expansion ($14 \times 10^{-6}$ $K^{-1}$) than PI2566. The materials of each layer of the flexible element 3 are chosen such that the distance moved by the flexible element 3 when heated is relatively large, e.g. it may be of similar dimensions to the size of the flexible element. For example, for a flexible element 3 of dimensions of the order of microns, materials are chosen such that the movement of the flexible element 3 is also of the order of microns. Polymers and/or metals can be used as the materials for the constituent layers of the flexible element 3.

A method based on controlled delamination of thin films from a substrate through forced variation is employed. This approach eliminates the need to protect layers from chemical degradation during a final etch release step and also allows freeing of arbitrary large areas.

The delamination technique is based on optical lithography and exploits the weak adhesion of gold to silicon, silicon dioxide or glass. By inducing stresses in constituent layers of the flexible element 3, then releasing it from an anchoring layer on substrate 2, it may curl at a non-fixed end, extending from the body region 2. Any of the three materials (silicon, silicon dioxide or glass) may be successfully used as the substrate 2, which (substantially) forms the body region 2.

A thin layer of Cr, Ni or N—Cr (500 Å) 2a is plasma sputtered onto the substrate 2 and acts as a first adhesion promoter between the substrate 2 and subsequently plasma sputtered gold barrier layer 2b (1000 Å). The gold barrier layer 2b is deposited to prevent oxidation of the adhesion promoter 2a upon exposure to air. The first adhesion promoter layer 2a and gold barrier layer 2b are then patterned to define the area from where the flexible element 3 will be released i.e. parts of the first adhesion promoter layer 2a are removed. Patterning is done using standard lithography and wet etching techniques, obtaining openings in the first adhesion promoter layer 2a for the later forced delamination of the flexible element 3. The pattern is essentially the inverse of the anchoring layer image i.e. material deposited above the region enclosed by the open ended rectangular structure will eventually form the flexible element 3, whereas material deposited about this region will form the anchoring layer from which the flexible element 3 will be released. The pattern is a thin track defining three sides of a rectangle of dimensions 500 µm by 80 µm, and thereby an 'open ended' rectangular structure. This effectively defines the size of the flexible element 3, which is also 500 µm by 80 µm. In being open ended, upon release, one end of the flexible element 3 remains fixed to the body region 2, while another is free to move, extending from the body region 2.

A gold structural layer (1.2 µm thick) 2c, 3a is then plasma sputtered on top of the patterned gold barrier layer (1000 Å). The gold structural layer acts only as a passive mechanical layer and is electrically insulated from a heater 4 by a polyimide layer 2d, 3b whose deposition is described herein below. In the same deposition run, a thin Cr layer (not shown) (<500 Å) is deposited over the gold structural layer to act as an adhesion promoter for a subsequent polyimide layer.

A polyimide layer of PI2566 2d, 3b is then spin coated over the gold structural layer 2c, 3a from the liquid phase and soft baked at 120° C. in an oven for 20 minutes. Thereafter, a 1500 Å thick Ni—Cr layer is sputter coated and patterned to form the heater tracks 4a, contact pads 4b and signal lines. Standard photolithography was carried out using positive tone photoresist to pattern the flexible element 3 and define contact pads. Patterning was done using wet chemical etching. However, an alternative technique would be reactive ion etching (RIE) of the polyimide layer. This would require a Cr layer to act as hard mask. Using similar techniques, a resistive Wheatstone bridge circuit 5 is also deposited, including a constituent piezoresistive element 5a and contact pads 5e, 5f.

Finally, following the final depositions, a wet Au etch is performed to release the flexible element 3 from the anchoring layer. Due to the initial stresses in the constituent layers of the flexible element 3, there is no need for special release recipes. The induced force prevents the flexible element 3 from sticking to the substrate 2. Thus, upon release, the flexible element 3 bends up and away from the body region 1.

The thickness of the gold structural layer 2c, 3a of the flexible element 3 (1.2 µm) was chosen to offer good actuation results. The value of 1.2 µm was empirically established. It was also established that for the mechanical properties of the constituent materials of the flexible element 3 (Gold, PI2566), a thickness ratio of 4:1 produced the greatest initial deflections, whereas a thickness ratio of 8:1 gave optimum experimental results. It will be appreciated that other thicknesses and ratios thereof could be employed. Also, thickness variation of the polyimide layer 2d, 3b can be achieved by varying the spin speed during spin coating. It will be appreciated that a second layer of PI2566 could be spin coated to embed the heater 4 structure for improved thermal insulation and also mechanical protection.

It will be appreciated that stress within constituent layers may be sufficient to cause, upon release, the flexible element 3 to bend so much that it curls back on itself, forming a 'roll' of material. Most preferably fabrication of the detecting device 1 is such that this situation is avoided, such that upon release, the flexible element 3 does not form such a roll. Preferably, the coefficients of thermal expansion of the constituent layers 3a, 3b of the flexible element 3 are different along the length of the flexible element 3 (defined by the distance from the point at which the flexible element 3 is fixed to the point at which it is free), but the same along the width of the element, such that the flexible element 3 bends along its length, but does not bend substantially across its width.

Figure 3:
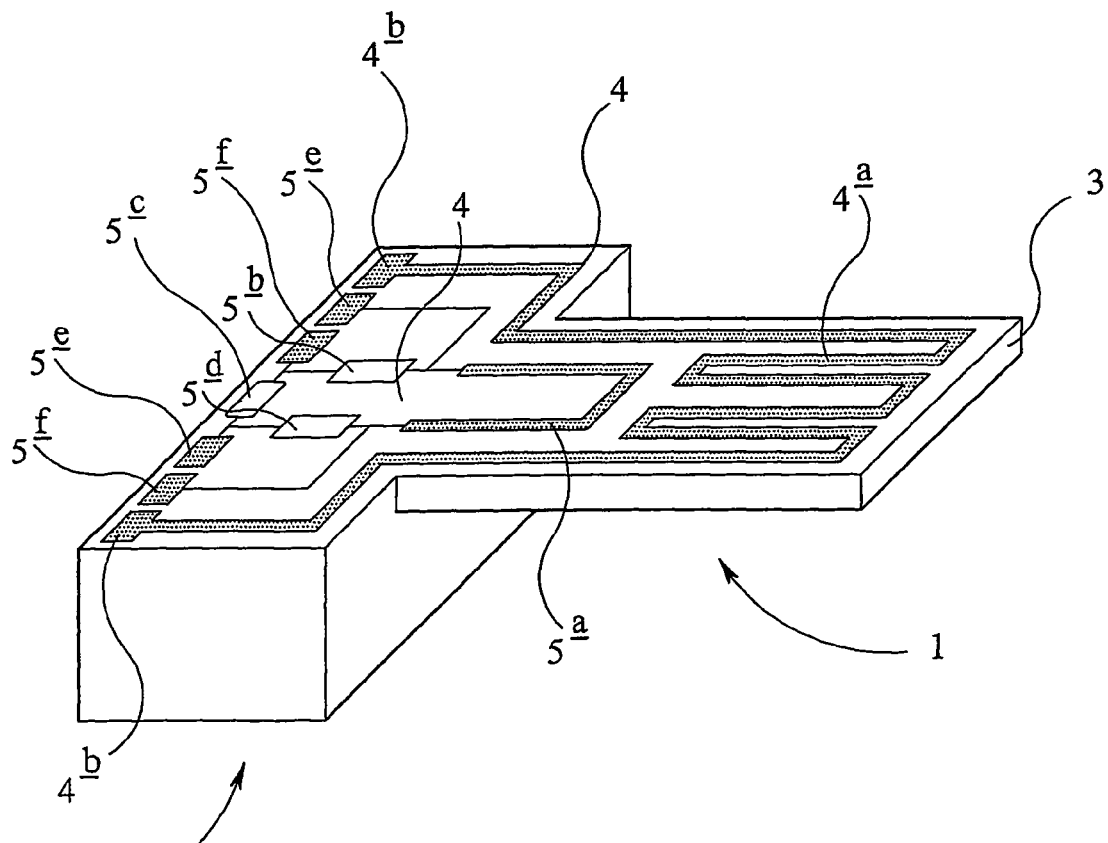
FIG. 3 is a simplified perspective view of the detecting device of FIG. 1.
Figure 4:
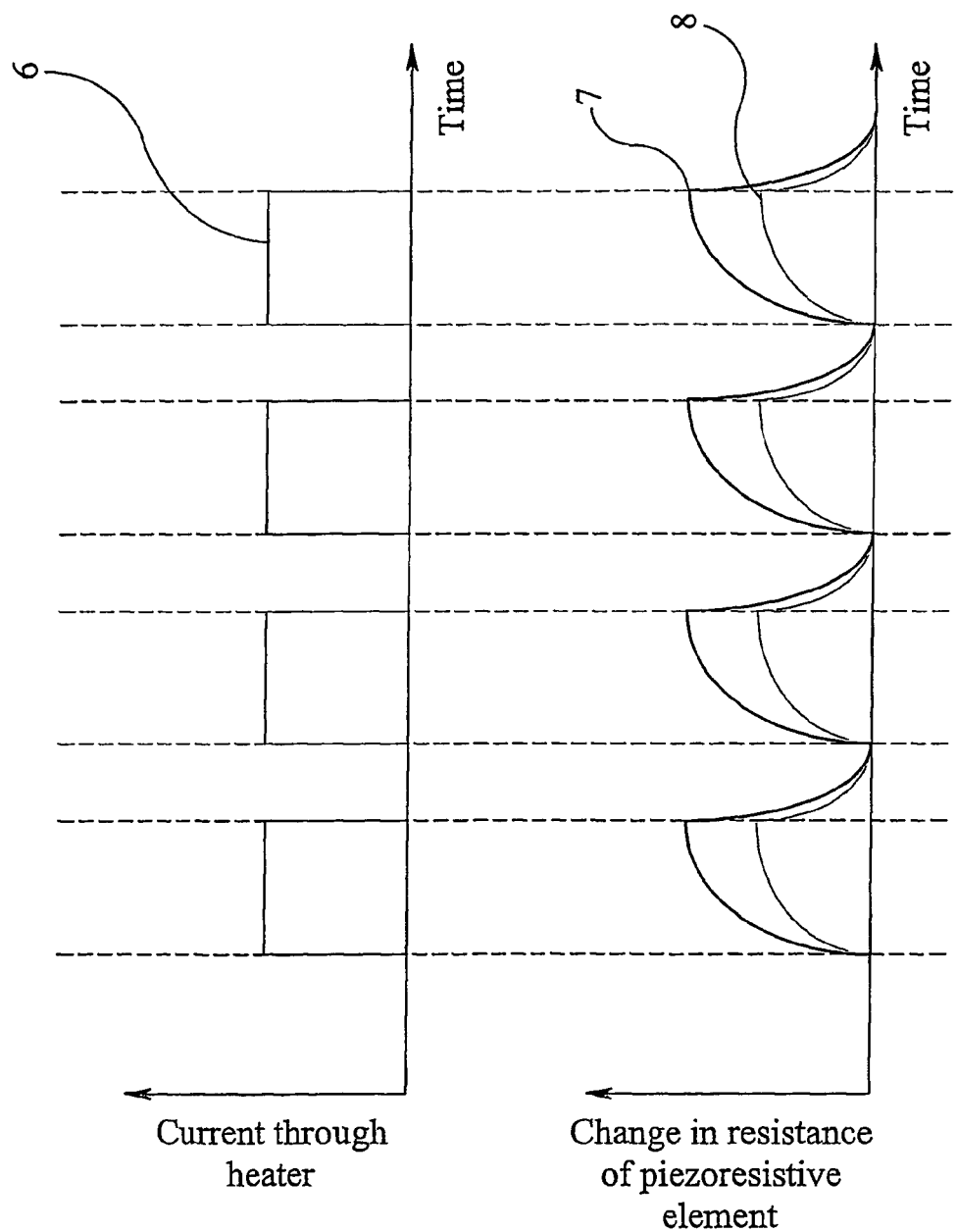
FIG. 4 is a graphical representation relating an input signal to a detecting device to the change in resistance of a constituent piezoresistive element.
Figure 5:
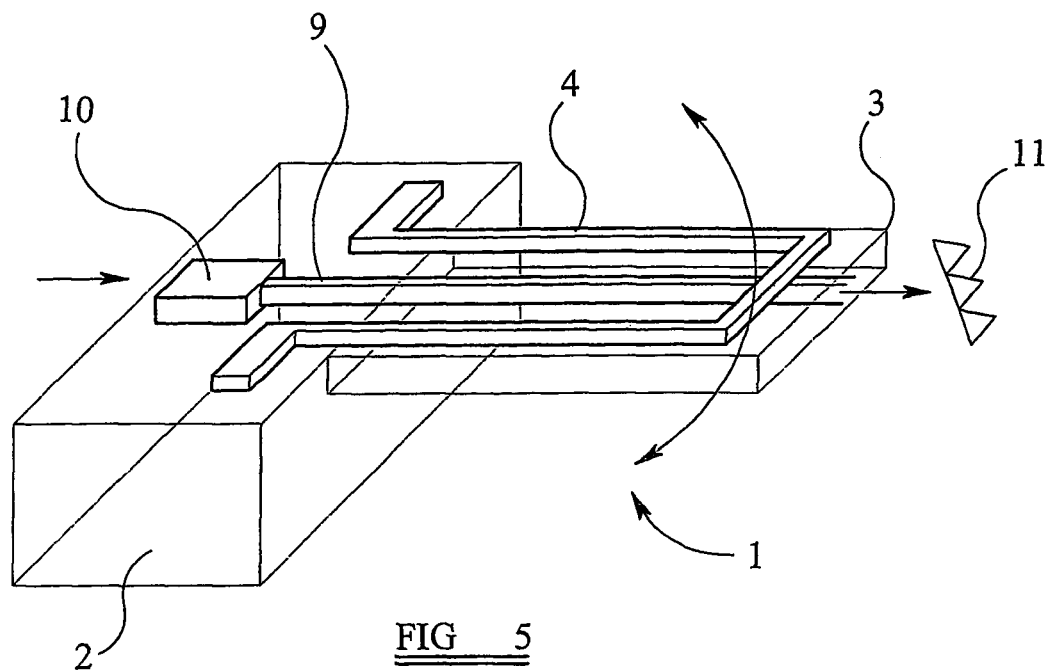
FIG. 5 is a perspective view of a detecting device in accordance with another embodiment.

For ease of description, use of the detecting device 1 is now described wherein the flexible element 3 is flat and unbent. Parts of the body region 2 not attached to and surrounding the flexible element 3 are no longer illustrated so as to highlight the flexible element 3. Additionally, FIGS. 3 to 5 are less detailed than FIG. 1, in so far as they do not illustrate constituent layers of the device 1. Similar parts are given the same reference numerals in each Figure.

When a current is made to pass though the track 4a of the heater 4 shown in FIG. 1, via the application of a potential difference across the heater contacts 4b, heat is dissipated due to electrical resistance in the track 4a. This heat causes the temperature of the flexible element 3 to increase. In heating the flexible element 3, one layer of the laminate 3b will expand at a greater rate than the other 3a due to the differential in their respective coefficients of thermal expansion. Hence, as illustrated in FIG. 3, the flexible element 3 will bend and become straighter—the flexible element 3 has been made to move from a first to a second configuration. The end of the flexible element 3 of this embodiment can move through a distance in the range 200 µm to 250 µm. In bending, the flexible element 3 induces a strain on the piezoresistive element 5a that will induce a change in its electrical resistance. Hence, in conjunction with the piezoresistive element, the Wheatstone bridge 5 can be used as a strain gauge, the output voltage of the Wheatstone bridge circuit 5 reflecting the (change in) electrical resistance of (and strain upon) of the piezoresistive element 5a.

For a given input signal to the heater 4 (a heat signal), the flexible element 3 will move (or 'deflect') a certain amount. If the heat signal is repetitive, varying from a 'current on' to a 'current low' or even 'current zero' value, the flexible element 3 will continue to bend when it is heated, and will relax towards its equilibrium position when no (or less) heat is applied to it, accordingly. The flexible element 3 will effectively oscillate. If a damping force is applied that opposes the movement of the flexible element 3, it will take longer to reach only maximum possible deflection for a given input. Further, if the heat signal is pulsed, the element may not reach this maximum deflection, as the element is bent in the other direction due to the change in heat signal. These effects can be used to detect and determine the viscosity of a fluid.

A more viscous fluid will have a greater damping effect on the movement of the flexible element 3 than a less viscous one. The change in deflection corresponds to a change in strain on the piezoresistive element 5a, which in turn alters it resistance. As the piezoresistive element 5a is a leg of a Wheatstone bridge 5, the change is reflected in a change of output voltage of the Wheatstone bridge 5. Thus, from the output of the Wheatstone bridge 5, the change in deflection can be directly measured, and this corresponds to a change in the viscosity of the fluid. FIG. 4 illustrates the effect of damping on the movement of the flexible element 3.

FIG. 4 has two graphs, one illustrating the current supplied to the heater 4 and a corresponding graph displaying the corresponding absolute change in the resistance of the piezoresistive element 5a in fluids of different viscosities 7, 8. A square wave signal 6 is applied to the heater 4, and therefore heat to the flexible element 3. The application of heat induces movement of the flexible element 3, which in turn causes a strain to be induced in the piezoresistive element 5a. Consequently, the resistance of the piezoresistive element 5a will change 7 with movement of the flexible element, which is directly related to the application of heat from the heater 4. By locating the flexible element 3 in a more viscous fluid, the movement of the flexible element 3 will be damped. The resistance of the flexible element 3 will change less rapidly in a more viscous fluid 8. Further, in the example shown, the amplitude of resistance is less in the more viscous fluid 8. The change in resistance can thus be used to determine a change in the viscosity of a fluid.

The resistance at the end of the signal pulse can be used to determine the maximum deflection, this maximum changing for fluids of different viscosities. However, it may be the case that the pulse duration (current 'on' time) is too great for the change in deflection to be resolved i.e. the flexible element 3 has the same maximum deflection in liquids of different viscosities for an identical input signal. This can be accounted for by varying the length of time for which current is applied to the heater 4 (and hence heat to the flexible element 3), and/or the magnitude of the current, and/or the period between successive current pulses. In short, the input signal can be tailored to the situation as appropriate.

Alternatively, the resistance of the piezoresistive element 5a is monitored continuously such that its change with respect to time can be observed. Hence, even if the resistance at the end of a pulse (i.e. the deflection of the flexible element 3) is the same, the rate of change of resistance will be different for fluids of different viscosities. The resistance of the piezoresistive element 5a will change more rapidly for a fluid of one viscosity than for a fluid with a second, higher viscosity. This is simply a consequence of the fact that, with a constant driving force, a body's movement is quicker through a less viscous liquid than for a fluid of a higher viscosity. Most preferably, the input signal is such that when no current is applied, the flexible element 3 is allowed to return to its equilibrium position i.e. dissipate all heat energy provided by the heater 4. Preferably, when no current is supplied to the heater 4, the heater 4 supplies no heat to the flexible element 3 i.e. the heater 4 dissipates heat extremely quickly. If the flexible element 3 is made to oscillate, preferably the frequency of the input signal is optimised to the dimensions of the flexible element. A high sampling rate (and hence high frequency oscillation) may be required for some applications. It will be readily appreciated that the same results can be achieved from a single input pulse, causing a single deflection of the flexible element 3, for each experiment.

As well as using the change in resistance/deflection to measure the viscosity of a fluid, the resonant frequency of the flexible element 3 can also be utilised for the same purpose. A resonant system is one in which a large oscillation is produced by a small stimulus of approximately the same frequency. The frequency at which this occurs for a given system is dependant upon the viscosity of the medium in which the oscillating part of the system is immersed. Thus, the flexible element 3 of the detecting device 1 will have an intrinsic resonant frequency unique to the fluid in which it is immersed. Thus, by varying the driving frequency (the input signal to the heater 4) of the flexible element 3, while simultaneously monitoring the resistance of the piezoelectric element 5a (and thus deflection of the flexible element 3), the amplitude of deflection of the flexible element 3 can be directly related to its driving frequency. Thus, the resonant frequency of the flexible element 3 can be readily identified, and the viscosity of the fluid derived therefrom.

With its strain and temperature sensitivity, it is clear to see that such a detecting device 1 has many applications other than the measurement of viscosity. For example, the device 1 can be used to measure temperature, flow rate and shear of a fluid.

As with the application of heat from the heater 4, environmental heat will cause the constituent layers of the flexible element 3 to expand/contract accordingly. This expansion/contraction induces a change in the strain on the piezoresistive element which is detectable from the output of the Wheatstone bridge circuit 5 of which it is a crucial part. Thus, monitoring the initial position of the flexible element 3, prior to it being driven by a heat signal from the heater 4, can be used to determine the temperature of the fluid.

It has already been described how the Wheatstone bridge circuit 5 effectively operates as a strain gauge, using the piezoresistive element's 5a inherent properties to achieve such functionality. If the flexible element 5a is placed in a flowing fluid a change in magnitude of the deflection of the flexible element 3 can be used to determine the flow rate of that fluid. The faster the flow of the fluid, the more constituent material per unit time is incident upon the flexible element 3 and thus the greater the force upon the flexible element 3. A greater force on the flexible element 3 results in a change in magnitude of deflection, for a given applied heat signal.

The properties of a fluid sample can be determined in a plurality of locations, thus determining a profile of said sample with respect to said property. For example, by measuring the flow rate of a fluid sample at a number of locations, a flow rate profile, and thus the shear rate, can be determined. One such way of achieving a profile is to use a single device 1 and move it through the sample, taking measurements at desired locations. However, this leaves the possibility that a property at a specific location may change between successive measurements, thus giving an inaccurate profile i.e. the property at the first location may change by the time a measurement at another location is made. Ideally, the measurements can be simultaneously taken at the desired number of locations. Preferably the measurements can be taken in real time. Real time measurement may yield further fluid sample information, such as the clotting time of blood. By using a plurality of detecting devices 1, preferably one for each desired measurement location, such real time, multi-location measurement and thus profiling can be achieved.

It is clear that use of such a detecting device 1 will yield only relative values of viscosity, temperature, etc. For example, an oscillating flexible element 3 will deflect substantially less in motor oil than in air. To obtain absolute values, calibration of the detecting device 1 and modelling of the fluid and/or flexible element 3 of the detecting device 1 may be required. For example, deflection of the flexible element 3 for a given input signal may be measured in one or more fluids of known viscosities, and from that, a specific change in deflection can be related to a specific change in viscosity. It will also be appreciated that accurate modelling of the flexible element 3 and its movement can yield properties about a fluid in which it is immersed. It will also be appreciated that there are a variety of interdependent factors that may have a measurable effect on a given measurement. For example, in heating the flexible element 3 to induce movement therein, some heat energy will undoubtedly be transferred to the fluid in which the device 1 is immersed. Such heat dissipation will raise the temperature of the fluid and may alter its viscosity, thereby giving a false measurement thereof. Similarly, the electrical resistance of the piezoresistive element 5a will change with temperature, the temperature itself being related to the temperature of the fluid plus any effects due to the heater 4. All of these problems may be overcome via a combination of calibration and/or modelling of the elements necessary to perform a desired measurement.

In another embodiment (not shown), the device 1 is generally similar to that described in relation to FIGS. 1 and 2. However, in this embodiment the Wheatstone bridge 5 now comprises capacitive elements as opposed to resistive elements, and the piezoresistive element has been removed. Instead, a conductive plate is located above, but not in contact with, the flexible element 3. Whereas in the device 1 of FIG. 1 a changing output signal resulted from a strain on, and corresponding change in electrical resistance of, a piezoresistive element, in this embodiment, changes in capacitance are used to detect movement of the flexible element 3. The Wheatstone bridge 5 comprises a known capacitance on each of three of its arms, and the conductive plate and flexible element 3 form the plates of a fourth (variable capacitance) capacitor. If the flexible element 3 moves, the separation between it and the conductive plate above will change and, from basic electrostatic theory, so will the capacitance of this fourth capacitor. This detector device 1 operates in an otherwise identical manner to, and has the functionality of, the detector device 1 of FIGS. 1 and 2.

It will be clear to one skilled in the art that all of the aforementioned embodiments are not restrictive in any way, and are given by way of example only. For example, all embodiments of the invention described thus far comprise a Wheatstone bridge 5 having four legs 5a, 5b, 5c, 5d, three of which 5b, 5c, 5d each comprise a constant and known value of resistance/capacitance. The fourth leg 5a comprises a variable resistance/capacitance sensitive to movement of the flexible element 3. By incorporating more movement sensitive resistances/capacitances in other legs of the Wheatstone bridge 5 (i.e. replacing the known and constant value components) the sensitivity of the bridge may be increased. The sensitivity of the Wheatstone bridge 5 is defined by the change in its output voltage for a small change in its input parameters i.e. variable resistance. If the output voltage can be made to be greater for the same or smaller change in its input parameters, its sensitivity is said to have increased. In comparison with the use of one leg, the use of two legs yields a two-fold increase in sensitivity, three legs a three-fold increase and four legs a four-fold increase. The incorporation of such additional movement sensitive resistances/capacitances can be achieved in a number of ways.

Taking a detecting device 1 incorporating a piezoresistive element for example, two legs of a Wheatstone bridge 5 may each comprise a piezoresistive element. The piezoresistive elements of two adjacent flexible elements may form two of the legs of the Wheatstone bridge. Alternatively, using only a single flexible element 3, another piezoresistive element (in addition to that residing on the flexible element 3 immediately adjacent the body region 2) may reside on the flexible element 3. By forming a Wheatstone bridge 5 utilising each piezoresistive element as a leg of the bridge, a more sensitive strain gauge is created. For example, an additional piezoresistive element may reside on the upper surface of the flexible element 3 at a point remote from the body region 2.

It will be appreciated that the piezoresistive element 5a may reside anywhere on the flexible element 3, so long as the strain that is under changes when the flexible element 3 moves. For example, the piezoresistive element 5a may be underneath the flexible element 3. The piezoresistive element 5a may reside on the flexible element 3 adjacent the body region 2 of the detecting device 1, at a point remote from the body region 2 or at a point somewhere in-between these extremes. The piezoresistive element 5a may reside on both the body region 2 and the flexible element 3 such that only a part thereof is under strain when movement is induced within the flexible element 3. The piezoresistive element 5a may be part of the flexible element 3. The piezoresistive element 5a may be a layer of the flexible element 3. It will also be clear to one skilled in the art that preferably, saturation of the piezoresistive element 5a is not encountered before maximum strain i.e. it has a unique electrical resistance for a unique applied strain (and associated movement of the flexible element 3)

Figure 6:
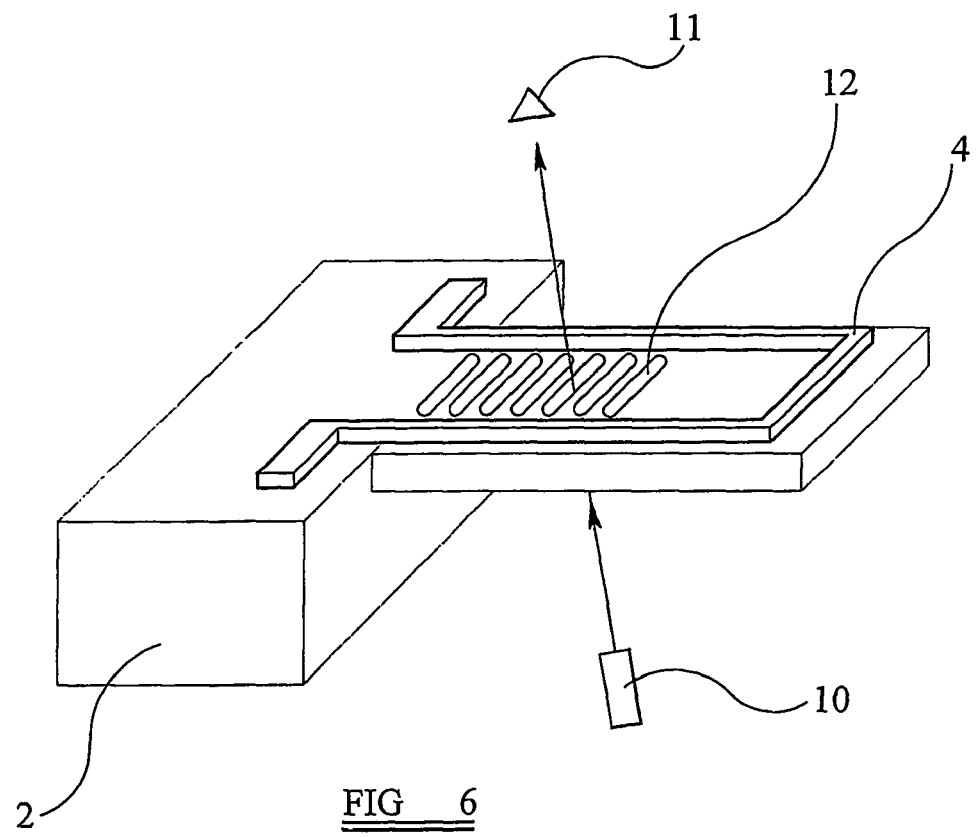
FIG. 6 is a perspective view of a detecting device in accordance with a further embodiment.

FIGS. 5 and 6 are perspective views of further embodiments of the current invention, again with flexible element 3 in a 'pre-stressed' state—initially straight. In these embodiments, detection of the movement of a flexible element 3 is undertaken using optical techniques, replacing the Wheatstone bridge circuits 5 and the variable capacitance/resistance elements of the aforementioned embodiments. Save for this replacement, the structure of the body region 2, heater 4 and flexible element 3 is identical to that described in relation to FIGS. 1 and 2, thus the functionality of these detection devices 1 remains unchanged. Hence, elements present in FIGS. 5 and 6 that are present in FIGS. 1 and 2 are given like reference numerals.

Referring to FIG. 5, the detecting device 1 comprises a body region 2, a flexible element 3, a heater 4 and a waveguide structure 9. The waveguide structure 9 is located within the detecting device 1, extending from the body region 2, through the flexible element 3 and to an outer surface of the flexible element 3 remote to the body region 2. An electromagnetic radiation source 10 is located within the body region 2, so as to irradiate an entrance to the waveguide 9 and cause electromagnetic radiation to be transmitted therethrough. The transmitted electromagnetic radiation will pass through the waveguide 9 and will be emitted from both the detecting device 1 and the waveguide 9 at the outer surface of the flexible element 3 remote to the body region 2. The emitted radiation may be detected by use of a photodiode array 11. The resolution of the photodiode array 11 can be tailored to the desired measurement resolution. For example, the smaller the diodes in the array 11 (or more densely packed they are) the higher its resolution, thus allowing a smaller movement in the flexible element 3 to be detected.

In use, heat is supplied to the flexible element 3 via the heater 4 (or by the local environment) so as to cause it to bend from its initially bent configuration towards a straight configuration. The degree to which the flexible element 3 bends is proportional to the number of photodiodes 11 that are excited and thus the movement of the flexible element 3 can be determined.

Referring now to FIG. 6, the detecting device 1 comprises a body region 2, a flexible element 3 and a heater 4. The flexible element 3 comprises a grating 12, the grating 12 being formed by transparent and opaque sections parallel to one another. The grating 12 extends along a substantial length of the flexible element 3, away from the body region 2. A photodiode array 11 is located on one side of the flexible element 3, and an electromagnetic radiation source 10 on an opposite side, such that electromagnetic radiation may be emitted from the source 10, be transmitted through the transparent sections of the grating 12 and be detected by the photodiode array 11. Depending on the size of the opaque and transparent sections (or 'pitch' thereof) the detecting device 1 can be used in one of two ways. The grating 12 may be used as a pure light filter, the shadow of the grating 12 falling on the photodiode array 11. Alternatively, the grating 12 can be configured so as to cause incident radiation to diffract. In diffracting, the electromagnetic radiation may constructively and destructively interfere with itself, thereby creating an interference pattern on the photodiode array 11. Most preferably the electromagnetic radiation source 10 is chosen so that the radiation it emits does not penetrate the opaque sections of the grating 12 i.e. visible light is most preferable to x-rays.

In use, heat is supplied to the flexible element 3 via the heater 4 (or by the local environment) so as to cause it to bend from its initially bent configuration towards a straight configuration. In bending, the pitch of the opaque and transparent sections will change. Such a change will have an effect on the electromagnetic radiation that is transmitted through the grating 12 and, depending on how the grating 12 is configured, either the shadow of the grating 12 or the interference pattern on the photodiode array 11 will change. Patterns in maxima and minima of the pattern/shadow can be used to determine the change in pitch of the sections of the grating 12, and this change is proportional to the movement (curvature) of the flexible element 3.

It will be appreciated that the transmissive grating 12 could be replaced with a reflective grating 12. The device 1 operates in exactly the same way, apart from the fact that the sections of the grating 12 are reflective and non-reflective, and the photodiode array 11 is on the same side as the electromagnetic radiation source 10, thereby detecting reflected, as opposed to transmitted electromagnetic radiation.

For all embodiments utilising optical detection methods, it will be appreciated that preferably the radiation source 10 and photodiode array 11 are chosen so as to compliment one another. For example, electromagnetic radiation from a source 10 with a peak emission wavelength of 640 nm (red light) may be best detected with a photodiode array 11 with peak sensitivity either at or near that wavelength. Furthermore, it will be appreciated that the photodiode array 11 can be one or two-dimensional. A two-dimensional photodiode array 11 can be used to image the transmitted/reflected electromagnetic radiation. For example, in the case of the embodiment comprising a grating 12, the entire fringe pattern may be detected with a two-dimensional array 11, whereas a one-dimensional array 11 will only yield information in a line across said fringe pattern. Although a one-dimensional analysis may be sufficient, the detection and capturing of a two-dimensional image may be of some use. It will be obvious to one skilled in the art that the photodiode array 11 may be replaced with any detecting element with the desired properties in terms of detection range, resolution etc. For example, the detection of electromagnetic radiation may involve optical fibres and associated processing means.

It will be obvious to one skilled in the art that all of the aforementioned embodiments are not restrictive in any way, and are given by way of example only. It will be clear that various modifications may be made to the detecting device 1 while not detracting from the invention.

For example, although the determination of fluid properties has been shown to incorporate the use of the flexible element 3 moving from a flat to curved position, or curved to flat position, other 'initial' and 'final' positions or 'configurations' of the flexible element are possible. The flexible element may move from a first curved configuration to a second curved configuration. In order to determine properties of a fluid, the flexible element must move from a first configuration to a second configuration. It may also move to other configurations thereafter. The first and second configurations may be the same.

Latching means may be provided to hold or 'latch' the flexible element 3 in a desired position. For example, if the flexible element 3 comprises a magnetic material (such as cobalt) an electromagnet located adjacent the device 1 can be used to latch the flexible element 3 in a desired position. Alternatively, a magnetic material may be fixedly attached to the flexible element. When the electromagnet is 'on' it may be arranged to attract the magnetic material and consequently the flexible element 3. Alternatively, it may be arranged to repel the electromagnet.

Whether the electromagnet generates an attractive or repellent force, if the flexible element 3 is resilient, a build up of potential energy in the flexible element 3 (due to elasticity of the element 3) may oppose the attractive or repelling magnetic force. Such a build up of energy can generate a restoring force that may attempt to restore the position of the flexible element 3 to its equilibrium position. If the magnetic force is such that it counterbalances the restoring force, the flexible element will be 'latched' in a desired position.

The electromagnet may be integral to the device or the electromagnet may be a separate piece of apparatus. Alternatively, the flexible element may comprise an electromagnet, and the magnetic material may be a separate piece of apparatus. It will be appreciated that any controllable source of variable magnetic field may be used instead of an electromagnet.

Figure 7:
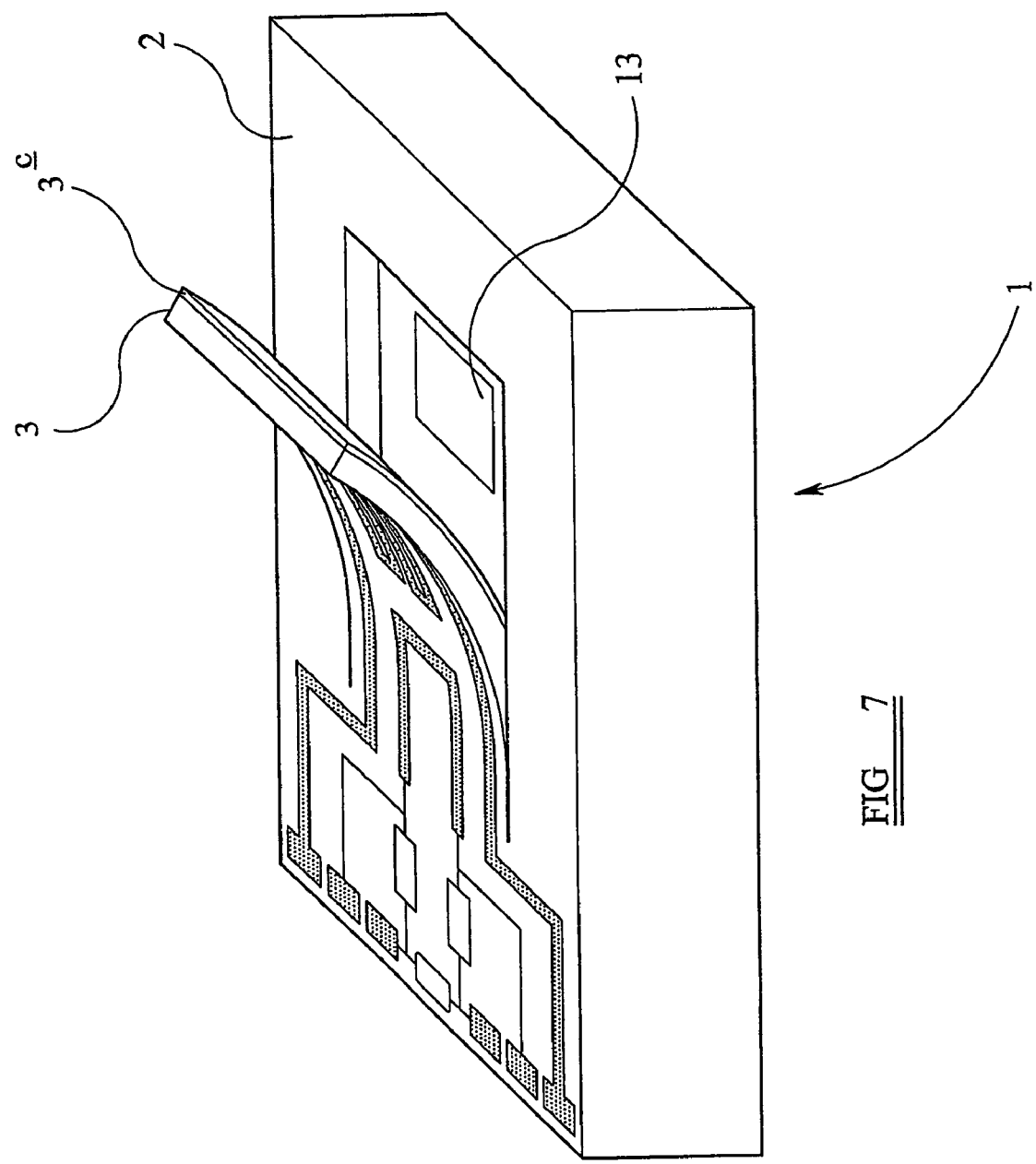
FIG. 7 is a perspective view of a detecting device in accordance with yet another embodiment.

In an alternative embodiment illustrated in FIG. 7, the flexible element 3 forms one plate of a capacitor like structure. The flexible element 3 comprises an electrically conductive layer 3c (such as gold) forming a first plate of the capacitor like structure. Another electrically conductive plate 13 (such as gold) forms a second plate of the capacitor like structure, and is located on the body region 2 of the device 1.

A potential difference applied between these two plates 3c, 13 causes opposing charges to build up on each plate 3c, 13, and an electric field is established between the plates. As opposite electrical charges attract, the plates 3c, 13 will be attracted toward each other. It will be appreciated that this attractive force (electrostatic force) can be used to hold or latch the flexible element 3 in a desired position. Preferably the second plate 3c is fixed in position, i.e. not free to move, to ensure that when latched, the flexible element does not move as a consequence of any movement of the second plate 3c.

If the flexible element 3 is resilient, a build up of potential energy in the flexible element 3 (due to elasticity of the element 3) may oppose the attractive electrostatic force. Such a build up of energy can generate a restoring force that may attempt to restore the position of the flexible element 3 to its equilibrium position. If the electrostatic force is such that it counterbalances the restoring force, the flexible element will be 'latched' in a desired position.

Electrical contact between the plates 3c, 13 is undesirable. The device 1 can be structured such that such electrical contact is not possible. For instance, the second plate 3c may reside in a recess in the body region 2 such that, even when the flexible element 3 is flat, the first 3c and second plates 13 are spatially separated and electrical contact therebetween prevented. Alternatively, in some embodiments, one (or each) of the plates is (are) coated in an electrically insulative layer (not shown) to prevent such electrical contact. The electrical insulator may be a plastic material.

It will be appreciated that the second plate 13 may not reside on the body region 2. For example, the location of the second plate 13 need only be such that an electric field may be established between the plates that is sufficient in magnitude to latch the flexible element 3 in a desired position.

Latching of the flexible element 3 has significant advantages. For example, the flexible element 3 is formed of (at least) two layers having different coefficients of thermal expansion. When heated, the flexible element 3 moves from a first configuration to a second configuration. An electric or magnetic field can then be applied to hold that flexible element 3 in position, whereafter the heat can be removed. The temperature of the flexible element 3 can then return to the ambient temperature of its surroundings i.e. the fluid in which it is immersed. The flexible element will then be resiliently biased to return to the first configuration. The electric or magnetic field can then be removed, allowing the restoring force due to the temperature change to move the flexible element 3, and the motion of the flexible element 3 to be characterised at this ambient temperature. Thus, the heat required to move the flexible element 3 does not affect the results of the experiment. Furthermore, the use of electric or magnetic fields to hold the flexible element 3 in position is more energy efficient than the use of heat (or current supplied to a heater), thus reducing the power consumption of a device incorporating such features.

As hereinbefore described, it will be appreciated that the capacitor like structure may also act as a variable capacitor. By applying a constant potential difference between the plates 3c, 13, the separation between the plates 3c, 13 can be extrapolated from the capacitance of the capacitor using simple electrostatic theory. If the separation of the plates 3c, 13 changes, so will the capacitance of the capacitor. Thus, as the flexible element 3 comprises one plate of the capacitor, the variable capacitor can be used to detect and characterise movement of the flexible element 3.

Furthermore, the flexible element 3 may not be a laminate of two materials. The flexible element 3 may comprise more than two materials and/or layers e.g. it can be formed of multiple layers of piezoresistive material, or any other desired material. It will be appreciated that the flexible element need only be capable of moving from a first to a second configuration when heated. Preferentially the movement is relatively large. This can be achieved by selecting materials with appropriate properties (such as certain Young's Modulus' and Coefficients of Thermal Expansion), such that a small applied heat signal generates a relatively large movement of the flexible element 3. This is preferentially achieved by the use of a laminate of two or more layers. One layers can comprise a polymer. One layer can comprise a metal. The polymer may be a polyimide, polyamide or acrylic polymer. The metal may be aluminium or gold. The relatively large movement may facilitate the use of movement detectors incorporating optical methods and/or apparatus.

It will be appreciated that the size of the detecting device 1 may be chosen to suit a specific application to the situation. It will be appreciated that the size of the flexible element 3 may be chosen to suit a particular application. For example, sizes may range from the order to micrometers to the order of millimetres e.g. 1 µm to 10 mm. The length of the flexible element, defined as the distance from the first to the second end, may be, for example, 100 µm to 1 mm. The shape of the flexible element 3 is also variable. For example, the flexible element 3 may taper away from the body region 2. The flexible element 3 may flare outwards and away from the body region 2. The flexible element 3 may not be one continuous object. For example, the flexible element 3 may be a thin rectangular layer with sections cut out thereof. This may be for hydrodynamic purposes or otherwise. The flexible element 3 may even comprise an additional element secured to an end remote to the body region 2, for example a paddle. The paddle may be integral to the flexible element 3. The inclusion of a paddle may be used to increase the surface area of the flexible element, which may, for example, increase the detection sensitivity of the device for flow and shear rate measurements.

The heater and movement detector element may be separate. Alternatively, the heater 4 and movement detector element may be combined such that a single element performs both of the functions thereof. If the heater 4 comprises a material that is piezoresistive, the heater 4 may also function as the piezoresistive element 5a of the movement detector. The combined heater-movement detector may comprise a single material, such as gold. The piezoresistive behaviour of gold may be greatly enhanced by the use of an elastic support layer, such as a polyimide layer.

In order to form such a combined multi-layer heater-movement flexible detector element, a polyimide track is deposited on the flexible element 3, followed by a gold layer on top of that track. It will be appreciated that many configurations are possible in order to realise a combined heater-movement detector element. In order to function, the heater-movement detector element must dissipate heat and exhibit piezoresistive behaviour.

The flexible element 3 can be constructed so as to be straight at equilibrium (no applied signal) using specific fabrication methods. For example, specific stresses may be induced in one or more layers during heated fabrication thereof.

The type, shape and location of heater 4 may be chosen to suit the situation or design criteria. For example, the heater 4 may be on the top surface of the flexible element 3. The heater 4 may be located on the underside of the flexible element 3. The heater 4 may be embedded within the flexible element 3. For example, the heater 4 may reside between layers if the flexible element 3 is a laminate structure. This may ensure that the majority of heat is dissipated in the flexible element 3, as opposed to a fluid sample. This has two advantages, namely that efficiency is increased and, more importantly, the temperature of the sample is not raised artificially and thereby adversely affecting measurement. The heater 4 may be an electrically conductive material that dissipates heat. The heater 4 may be a separate device such as a non-integrated electrically conducting filament. The heater 4 may be a thin-film deposition of an electrical conductive material. The heater 4 may be a track of a conductive material. For example, the heater 4 may be an electrically conductive track that weaves along, and back and forth across the flexible element 3, thereby creating a uniform dissipation of heat thereon.

Cooling elements can also be employed on the flexible element 3. By incorporating coolers, the flexible element 3 could be made to bend using differential expansion of constituent layers of a laminar flexible element 3 if those layers possessed different coefficients of thermal expansion. The direction of movement would be opposite to that when heat is applied to the flexible element 3.

The detecting device 1 may also comprise a combined heater and cooler for heating/cooling of the fluid itself, such that measurements may be made at selected temperatures. This heater and cooler may reside on the body region 2 or on the flexible element 3. A movement (e.g. current) signal applied to the heater 4 may be any predetermined function. For example, the signal may be a sine wave, a modulated sine wave, a square wave, a single pulse or a continuous current of a constant value.

It will be clear that by using a plurality of flexible elements 3 simultaneously, a plurality of measurements can be simultaneously made. For example, using three independent flexible elements 3, the temperature, viscosity and flow rate of a fluid sample can be measured simultaneously. A plurality of devices 1 may be used in order to obtain the desired number of flexible elements 3, each device comprising one or more flexible element 3. Alternatively, a single device 1 comprising the desired number of flexible elements 3 (appropriately configured) may be used. The flexible elements 3 may be in any desired configuration. For example, two rows of the flexible elements 3 may be interdigitated.

A spatial profile of the properties of a fluid can be obtained by using a plurality of flexible elements 3/devices 1 located at different positions within the fluid. Thus, by using a device 1 comprising a plurality of flexible elements 3, such a profile can be readily obtained. It will be appreciated that such a profile can be obtained in real-time. For example, by measuring the flow rate of a fluid at a plurality of locations, the shear rate of the fluid may be obtained. By obtaining profiles in real-time, changes therein can be accurately determined. Such changes may be natural, for example the loss of heat energy, or induced, for example the introduction of a chemical to the fluid.

It will be appreciated that, just as a fluid can have an influence on a flexible element 3, a flexible element 3 may have an influence on the fluid. For example, movement of a flexible element 3 in a fluid may cause turbulence therewithin. Movement of a flexible element 3 in a fluid may also cause flow therewithin. Co-ordinated and specific movement of a plurality of flexible elements 3 can cause a specific flow in the fluid. Thus, flow can be artificially induced in a fluid. For example, flow can be induced in a fluid in order to simulate the flow of that fluid in a pipe. Properties of the fluid may then be determined while the fluid is undergoing such flow.

Using a plurality of flexible elements 3, some of the plurality may cause flow within a fluid e.g. by cyclically operating the elements 3. One or more other elements 3 may be used to characterise that flow. For example, a device may comprise seven flexible elements 3 arranged into two rows. The first row may comprise a first, third, fifth and seventh flexible element 3, and the second row a second, fourth and sixth flexible element. The flexible elements of the first row may extend in a first direction. The flexible elements of the second row may extend generally in a direction parallel but opposite to the first direction. Thus, the flexible elements of the first row are in opposition to those of the second row. In this embodiment, the seven flexible elements are interdigitated. The first, third, fifth and seventh flexible element 3 may be arranged to generate a flow within a fluid.

For example, movement of the first, third, fifth and seventh flexible element 3 can be controlled such that the movements 'cascade'. As the first element is made to move from the first to the second configuration, the third element 3 is made to move from the second to the first configuration, and as the third element 3 is made to move from the first to the second configuration, the fifth element 3 is made to move from the second to the first configuration etc. While the first, third, fifth and seventh flexible elements generate flow in the fluid, the second, fourth and sixth elements can be used to characterise that flow. For example, they can be used simultaneously to determine the shear rate of the fluid. Alternatively, or additionally, they can be used to determine different properties. For example, the second flexible element 3 may determine temperature of the fluid, the fourth flexible element 3 the fluid viscosity, and the flow rate may be determined by the sixth flexible element.

The device 1 may reside in a container such that environmental conditions within the container may be accurately monitored and controlled. For example, pressure and/or temperature within the container may be monitored and/or controlled. Such monitoring may be implemented and control exerted upon on any fluid residing within the container. It will be appreciated that only the flexible element(s) 3 of the device 1 may reside within the container, with the body region 2 of the (or each) device 1 residing outside of the container. Control or knowledge of the temperature of the fluid is useful when the viscosity of the fluid is being measured. This is especially true in the measurement of blood viscosity, as the viscosity of blood varies significantly with changes in temperature. Thus, temperature controlling and sensing devices may be used to actively control the temperature of the fluid within the container. For example, heaters and/or coolers may be used. The heaters and/or coolers may be independent apparatus, completely separate from the sensing device 1. Alternatively, the heaters and/or coolers may be integral to the sensing device 1. The temperature sensing device may also be separate from or integral to the sensing device 1. It will be readily appreciated that the temperature sensing device may be a flexible element 3 comprising layers of material with different coefficients of thermal expansion, as hereinbefore described.

It will be appreciated that the detecting device 1 may form an integral part of a larger, more complex system. For example, due to its ease of manufacture, the detecting device 1 can be fabricated at a low cost, which introduces the possibility of a readily disposable device 1. Although when determining properties of, for example, water the device 1 may or not need to be reusable, it is ideal in some circumstances that the device 1 is disposed of after a single use. This may be the case for a number of reasons, for example hygiene, contamination etc. A scenario where hygiene and contamination are of critical importance is the area of blood testing, and in particular the testing of human blood. This device 1 can be fabricated in extremely small sizes and thus it can be easily integrated into a blood extraction and testing system. Furthermore, due to the small size, a correspondingly small fluid sample is required.

For example, blood viscosity is related to deep vein thrombosis which has in turn been related to long-haul aeroplane flights. Ideally, a passenger could measure the viscosity of his/her own blood and therefore determine whether any blood-thinning agent needed to be taken (e.g. aspirin). The device 1 (or more than once device 1) could be integrated with a microneedle (for painless extraction of blood), and have readily detachable electrical connections that are designed to engage like connections on a small, handheld processing terminal. A needle and device 1 could be attached and thereby electrically connected to the terminal, and the passenger could painlessly extract blood from his/herself. Controlled by the terminal, the device 1 would then operate as described hereinabove, and yield information about the blood. The terminal could include a simple display with information such as the viscosity of the blood, whether it was at a dangerous level etc. Being small and cheap, the needle and device 1 could then be disposed of with little cost. The terminal could be used again with another needle and device 1. Hence, many devices 1 may be used on a single flight.

It is clear that the functionality of the device 1, together with its small size and low cost of fabrication make its use advantageous in a wide variety of applications where the determination of fluid properties, for example viscosity, temperature, flow rate and shear rate, is required. Preferably the fluid is a liquid. Preferably the liquid is blood or a constituent part thereof, such as plasma. Preferably the volume of fluid from which its properties are determined is of the order of 1 microlitre.

The invention claimed is:

1. A method of determining a property of a liquid using a sensing element comprising:
   providing a flexible element having a first end and a second end and being movable from a first configuration to a second configuration via bending of said flexible element, said flexible element comprising an actuating portion arranged to move said flexible element between said first configuration and said second configuration, the flexible element having a length from the first end to the second end, the actuating portion being distributed along the length, a first section of the actuating portion being proximate the first end, and a second section of the actuating portion being proximate the second end;
   inducing movement in said flexible element between said first configuration and said second configuration by applying a heat signal to said flexible element, the movement of the second end of the flexible element between said first and second configurations being at least 30 μm;
   receiving a signal from said sensing element, said signal being indicative of the induced movement of the flexible element within the liquid; and
   processing said signal to determine a value indicative of at least one property of the liquid.

2. A method as claimed in claim 1, wherein said actuating portion of said flexible element comprises a laminate of at least two layers, each layer having a different coefficient of thermal expansion, and wherein, prior to induction of movement by application of the heat signal, a value indicative of the temperature of the liquid is determined.

3. A method as claimed in claim 1, wherein the device comprises a plurality of flexible elements, such that the plurality of flexible elements may be used to determine a value indicative of at least one property of the liquid in a plurality of locations.

4. A method as claimed in claim 1, wherein the device comprises a plurality of flexible elements, at least one of the plurality being used to cause a flow within the liquid, and at least one of the plurality being used to determine a value indicative of at least one property of the liquid.

5. A method as claimed in claim 1, further comprising holding the flexible element in at least one of said two configurations by a magnetic force.

6. A method as claimed in claim 1, further comprising holding the flexible element in at least one of said two configurations by an electrostatic force.

7. A method as claimed in claim 1, wherein said received signal is indicative of a maximum deflection of the flexible element, said signal being processed to determine the viscosity of the liquid.

8. The method of claim 1 wherein the length of the flexible element from the first end to the second end is between 100 μm and 1 mm.

9. A method as claimed in claim 1, wherein said signal is processed to determine a value indicative of at least one property of a group comprising viscosity, temperature, flow rate and shear rate.

10. A method as claimed in claim 9, further comprising:
    determining a rate of change of movement of said flexible element, by monitoring a change in the received signal with time; and
    determining a value indicative of the viscosity of the liquid from said rate of change of movement.

11. A method as claimed in claim 9, further comprising:
    determining an amplitude of movement of said flexible element from said received signal for a given applied heat signal; and
    determining a value indicative of the viscosity of the liquid from said amplitude.

12. A method as claimed in claim 9, further comprising:
    determining a change in said movement of said flexible element; and
    determining a value indicative of a flow rate of the liquid from said change in movement, said change in movement being due to flow of the liquid against said flexible element.

13. A method as claimed in claim 12, further comprising: determining a value indicative of a shear rate of the liquid by determination of the flow rate at a plurality of locations within the liquid.

14. A device for detecting a property of a liquid comprising:
    a body region;
    a flexible element having a first end and a second end, said first end being fixedly located on said body region, said flexible element being arranged to move from at least a first configuration to a second configuration via bending of said flexible element, the second end of the flexible element moving at least 30 μm between said first and second configurations;

said flexible element including a laminate of at least two layers and an actuating portion arranged to move said flexible element between said first configuration and said second configuration, the actuating portion being provided by at least a first layer of said laminate having a different coefficient of thermal expansion from a second layer of said laminate such that a change in temperature of said flexible element moves the flexible element from said first configuration to said second configuration;

said flexible element further including a heating element for heating at least said flexible element and providing a change in temperature;

a movement detector arranged to detect said movement of said flexible element, and to provide a signal indicative of a property of a liquid in which the flexible element is immersed; and wherein said flexible element has a length from the first end to the second end, and said actuating portion is distributed along the length, a first section of said actuating portion being proximate the first end, and a second section of said actuating portion being proximate the second end.

15. A device as claimed in claim 14, further comprising latching means arranged to hold the flexible element in at least one of said two configurations.

16. A device as claimed in claim 14, wherein said movement detector comprises an electromagnetic radiation source arranged to direct radiation towards said element, and an electromagnetic radiation detector arranged to detect electromagnetic radiation at least one of: reflected from, transmitted through, refracted from or diffracted by said flexible element.

17. A device as claimed in claim 14, wherein the length of the flexible element from the first end to the second end is between 100 μm and 1 mm, and wherein the distance between the second end of the flexible element in said first configuration and the second end of the flexible element in said second configuration is between 30 μm and 650 μm.

18. A device as claimed in claim 14, wherein at least one of the first and second layers of said laminate comprises a polymer.

19. A device as claimed in claim 18, wherein at least one of the first and second layers of said laminate comprises a material selected from a group consisting of polyimides, polyamides and acrylic polymers.

20. A device as claimed in claim 14, wherein the second layer of said laminate comprises a metal.

21. A device as claimed in claim 20, wherein the metal is selected from a group consisting of gold or aluminium.

22. A device as claimed in claim 14, wherein said movement detector comprises a piezoresistive element located on said flexible element arranged such that the electrical resistance of the piezoresistive element changes due to movement of said flexible element.

23. A device as claimed in claim 22, wherein said piezoresistive element is located on the flexible element at a position remote from the body region.

24. A device as claimed in claim 22, wherein said piezoresistive element is formed as a layer of the laminate of said flexible element.

25. A device as claimed in claim 14, wherein the device comprises a plurality of flexible elements.

26. A device as claimed in claim 25, wherein the plurality of flexible elements are arranged in a first row and a second row, each row comprising at least one flexible element, the flexible elements being arranged such that the at least one flexible element of the first row extends in opposition to the at least one flexible element of the second row.

27. A device as claimed in claim 26, wherein the plurality of flexible elements are interdigitated.

* * * * *